(12) United States Patent
Clark et al.

(10) Patent No.: US 6,878,166 B2
(45) Date of Patent: Apr. 12, 2005

(54) METHOD AND IMPLANT FOR SECURING LIGAMENT REPLACEMENT INTO THE KNEE

(76) Inventors: Ron Clark, 4805 Lakeridge Ct., Valparaiso, IN (US) 46383; Raymond E. Olsen, 791 Canyon Ter., Smithfield, UT (US) 84335

( * ) Notice: Subject to any disclaimer, the term of this patent is extended or adjusted under 35 U.S.C. 154(b) by 495 days.

(21) Appl. No.: 10/061,094

(22) Filed: Feb. 1, 2002

(65) Prior Publication Data

US 2002/0087160 A1 Jul. 4, 2002

Related U.S. Application Data

(63) Continuation of application No. 09/942,111, filed on Aug. 28, 2001, now abandoned.
(60) Provisional application No. 60/228,357, filed on Aug. 28, 2000.

(51) Int. Cl.$^7$ .................................................. A61F 2/08
(52) U.S. Cl. ...................................... 623/13.12; 606/72
(58) Field of Search ............................... 606/60, 62, 72, 606/73, 75; 623/13.12

(56) References Cited

U.S. PATENT DOCUMENTS

| | | | | |
|---|---|---|---|---|
| 461,621 | A | * | 10/1891 | Rogers ........................ 411/424 |
| 4,338,054 | A | * | 7/1982 | Dahl ........................... 411/424 |
| 4,756,307 | A | * | 7/1988 | Crowninshield ............. 606/67 |
| 4,950,270 | A | | 8/1990 | Bowman et al. |
| 4,985,032 | A | | 1/1991 | Goble |
| 5,026,374 | A | * | 6/1991 | Dezza et al. ................... 606/72 |
| 5,098,435 | A | | 3/1992 | Stednitz et al. |
| 5,100,405 | A | * | 3/1992 | McLaren ....................... 606/72 |
| 5,139,520 | A | | 8/1992 | Rosenberg |
| 5,266,075 | A | | 11/1993 | Clark et al. |
| 5,300,077 | A | | 4/1994 | Howell |
| 5,350,380 | A | | 9/1994 | Goble et al. |
| 5,354,300 | A | | 10/1994 | Goble et al. |
| 5,356,413 | A | | 10/1994 | Martins et al. |
| 5,393,302 | A | | 2/1995 | Clark et al. |
| 5,397,356 | A | | 3/1995 | Goble et al. |
| 5,423,823 | A | | 6/1995 | Schmieding |
| 5,431,651 | A | | 7/1995 | Goble |
| 5,562,671 | A | | 10/1996 | Goble et al. |
| 5,593,408 | A | * | 1/1997 | Gayet et al. .................. 606/61 |
| 5,601,562 | A | | 2/1997 | Wolf et al. |
| 5,918,604 | A | | 7/1999 | Whelan |
| 6,132,433 | A | | 10/2000 | Whelan |
| 6,267,766 | B1 | * | 7/2001 | Burkhart ....................... 606/72 |
| 6,306,138 | B1 | | 10/2001 | Clark et al. |
| 6,623,524 | B2 | * | 9/2003 | Schmieding ............. 623/13.14 |
| 6,752,830 | B1 | * | 6/2004 | Goble et al. ............. 623/13.14 |
| 6,780,188 | B2 | * | 8/2004 | Clark et al. ................... 606/73 |
| 2001/0053934 | A1 | | 12/2001 | Schmieding |

* cited by examiner

Primary Examiner—Ralph A. Lewis
(74) Attorney, Agent, or Firm—Clayton, Howarth & Cannon, P.C.

(57) ABSTRACT

A surgical method and implant for directing and securing a replacement ligament into the femur or tibia of the knee. A transverse tunnel may be formed in the femur approximately perpendicular to a femoral tunnel. A flexible strand passing through the transverse tunnel may be used to draw the replacement ligament into the femoral tunnel. The implant may then be placed into the transverse tunnel and through the replacement ligament to secure the replacement ligament in place. The implant may include an eyelet to receive the flexible strand and a tapered portion forming a shoulder to prevent the implant from being inserted too far into the transverse tunnel. The implant may also have a multi-angular configured portion to secure the implant within the transverse tunnel through an interference fit.

27 Claims, 8 Drawing Sheets

METHOD AND IMPLANT FOR SECURING LIGAMENT REPLACEMENT INTO THE KNEE

CROSS-REFERENCE TO RELATED APPLICATIONS

This application is a continuation of U.S. patent application Ser. No. 09/942,111, filed Aug. 28, 2001, now abandoned, entitled "METHOD AND IMPLANT FOR SECURING LIGAMENT REPLACEMENT INTO THE KNEE," which is hereby incorporated by reference herein in its entirety, including but not limited to those portions that specifically appear hereinafter, which application claims the benefit of U.S. Provisional Application No. 60/228,357, filed Aug. 28, 2000, which is also hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates to the placement and fixation of a knee ligament replacement in tunnels formed in a longitudinal direction through the tibia and femur bones. The method of the present invention relates more particularly, but not entirely, to a method of securing the ligament replacement in a reliable manner that facilitates biological healing of replacement material into the bone.

2. Description of Related Art

When a ligament such as the anterior cruciate ligament (hereinafter "ACL") or posterior cruciate ligament (hereinafter "PCL") is torn or damaged, a replacement ligament may be used to reconstruct the natural ligament. A variety of biologic and synthetic materials have been developed for this purpose. In order to install the replacement ligament, tunnels may be drilled in a longitudinal fashion into the "footprints" of the native ligament positions to replicate the function of the natural ligament. Such techniques are well known and are in common domain.

Various methods and devices have been devised for the purpose of both placing and securing a ligament replacement into bone depending on the specific characteristics of the material. E. Marlowe Goble first devised a drill guide that would direct a drill point transversely to a bone tunnel drilled longitudinally into a knee bone. See U.S. Pat. No. 4,985,032. Thereafter, a means was devised for securing a soft ligament replacement into the femur by passing the tendons over a pin placed transversely across the femoral tunnel. See U.S. Pat. Nos. 5,266,075 and 5,393,302. Goble and Jerry L. Lower then designed a method and implant for securing a bone plug in the tunnel. See U.S. Pat. Nos. 5,350,380 and 5,397,356 and 5,562,671. Other inventors such as Thomas Rosenberg, see U.S. Pat. No. 5,139,520, have used soft tissues and transverse devices to secure ligament grafts into the femur. Replacement ligaments can also be secured with "interference" bone screws such as described by Jerald Bowman et al., see U.S. Pat. No. 4,950,270, or a whole combination of sutures tied to posts, staple type devices, and screw plates.

Ultimately, rounded cannulated implants were developed that allowed for a soft ligament implant to be first captured by a wire, see U.S. Pat. No. 5,918,604 (Jeffery Whelan), and brought in the tunnel of the femur and then secured by passing the cannulated implant along the path of the wire, see U.S. Pat. No. 5,431,651 (E. Marlowe Goble), thus securing the graft.

The prior art does not address certain challenges in the field discussed above. The prior art is thus characterized by several disadvantages that are addressed by the present invention. The present invention minimizes, and in some aspects eliminates, certain disadvantages and problems, by utilizing the methods and structural features described herein.

BRIEF SUMMARY OF THE INVENTION

The invention includes a surgical method and implant for directing and securing a replacement ligament into the femur or tibia of the knee. Utilizing bone tunnels in the femur and tibia, a step drill may be directed through a cannulated drill guide located in the femoral tunnel to the opposite cortex. A flexible strand may be brought into the femoral tunnel through the joint and retrieved from the transverse tunnel, the flexible strand forming a loop external to the joint. One end of the flexible strand may be directed through a medial transverse opening of the transverse tunnel and the other through a lateral transverse opening. Tensioning of the flexible strand causes the replacement ligament material to be drawn into the femoral tunnel. A novel implant described herein may then be passed into the transverse tunnel, passing through the ligament replacement and securing the ligament replacement within the femoral tunnel. A reverse method may be utilized to secure the tibial end of the ligament replacement.

The implant may include an eyelet to receive the flexible strand and a tapered portion forming a shoulder to prevent the implant from being inserted too far into the transverse tunnel. The implant may also have a multi-angular configured portion to secure the implant within the transverse tunnel through an interference fit.

Additional advantages of the invention will be set forth in the description which follows, and in part will be apparent from the description, or may be learned by the practice of the invention without undue experimentation. The advantages of the invention may be realized and obtained by means of the instruments and combinations particularly pointed out in the appended claims.

BRIEF DESCRIPTION OF THE DRAWINGS

Certain features and advantages of the invention will become apparent from a consideration of the subsequent detailed description presented in connection with the accompanying drawings in which.

DETAILED DESCRIPTION OF THE INVENTION

Figure 1A:
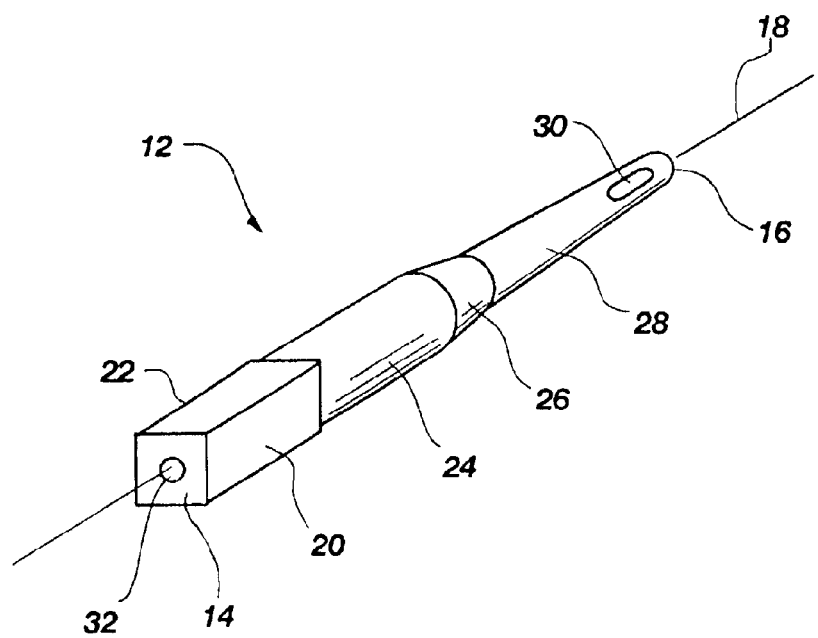
FIG. 1A is a perspective view of an implant in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present components and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference herein. The references discussed herein are provided solely for their disclosure prior to the filing date of the present application. Nothing herein is to be construed as a suggestion or admission that the inventors are not entitled to antedate such disclosure by virtue of prior invention.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

As used herein, "consisting essentially of" and grammatical equivalents thereof limit the scope of a claim to the specified materials or steps and those that do not materially affect the basic and novel characteristic or characteristics of the claimed invention.

The method of the present invention allows for the successful placement of a transversely placed implant into the femur to secure a flexible ligament graft used in the reconstruction of the anterior cruciate ligament.

The novel implant and method of graft fixation of the present invention provides multiple advantages over the previous methods and implants described above. The current implant may be of a solid form with a distal portion and a body portion attached to a multi-angular end portion. The distal portion may include an eyelet for the placement of a suture or other flexible material used in directing the implant around the replacement ligament. The implant may be secured into bone by impacting the multi-angular end, that has a slightly larger external dimension than the transverse round hole into the corresponding bone, and making it flush with external bone cortex. The compressive forces inherent to the geometrical mis-match between the implant and the transverse tunnel, secure the implant in place. The geometry of the present implant allows for a smaller profile and leads to the applicability of materials not heretofore utilized in transverse ligament fixation.

Certain aspects of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

Referring now to FIG. 1, a perspective view is shown of an implant, generally indicated at 12, in accordance with the principles of the present invention. The implant 12 preferably includes a proximal end 14, a distal end 16 and defines a longitudinal axis 18. The implant 12 may be constructed of any suitable material such as metal, polymer, or bone that is preferably inert or biologically compatible. The implant 12 is preferably substantially solid, characterized by the absence of a cannulation along the longitudinal axis 18.

The implant 12 may include a multi-angular portion 20 at the proximal end 14. The multi-angular portion 20 preferably has a polygonal cross section which may form a square for example. It will be appreciated that the multi-angular portion 20 may be formed of various different polygonal shapes, such as triangular, pentagonal, hexagonal, etc., within the scope of the present invention. The multi-angular portion 20 preferably forms a plurality of ridges 22 which extend substantially parallel to the longitudinal axis 18. The multi-angular portion 20 is preferably configured to have a slightly larger cross section than a hole in the bone receiving the implant 12 such that an interference fit is formed between the bone and the ridges 22 to hold the implant 12 in place. An interference fit as used herein refers to an abutting contact between two objects to prevent the two objects from moving with respect to each other in a particular direction.

The multi-angular portion 20 may also include a fitting 32 on the proximal end 14 for receiving a driver 54 (see FIG. 5A) to drive the implant 12 into the bone. The fitting 32 may be formed as a recess that is configured to receive a projecting tip 56 of the driver 54 to maintain contact between the driver 54 and the implant 12 while the implant 12 is being driven into the bone.

In an alternative embodiment of the implant 12, the multi-angular portion 20 may be replaced with a threaded portion (not shown). The threaded portion may have a cylindrical configuration with threads on the exterior surface to grip the receptor bone for fixing the implant 12 in place.

The implant 12 may also include a body portion 24 adjoining the multi-angular portion 20. The body portion 24 may have a cylindrical configuration which may have a slightly smaller radial dimension than the multi-angular portion 20 such that the ridges 22 extend radially beyond the body portion 24, as is clearly shown in FIG. 1B. The body portion 24 is preferably configured to facilitate insertion of the implant 12 within a bone. Thus, the surface of the body portion 24 is preferably substantially smooth, without threads or ridges for example.

Figure 1B:
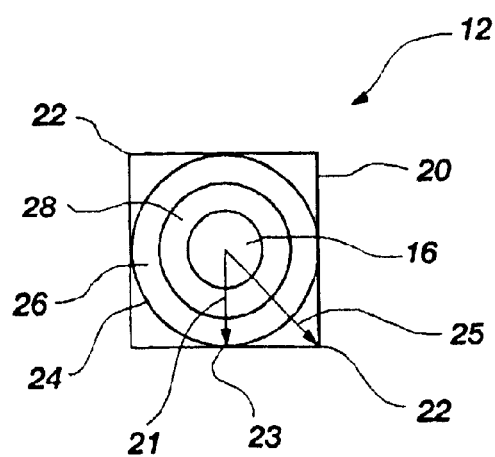
FIG. 1B is an end view of the implant of FIG. 1A, with radial reference lines.

In one embodiment of the present invention shown in FIG. 1B, a radial dimension 21 of the body portion 24 is substantially equal to a radial dimension of the multi-angular portion 20 at a point 23 between the ridges 22, whereas a radial dimension 25 of the multi-angular portion 20 at the ridges 22 is larger than the radial dimension 21 of the body portion 24. This relationship of sizes helps the insertion of the implant 12, since a smooth transition exists between the body portion 24 and the multi-angular portion 20 at the point 23 between the ridges 22. Furthermore, the larger radial dimension 25 of the ridges 22 provides an interference fit between the ridges 22 and the receptor bone when the implant 12 is installed. It will be appreciated however, that other radial dimensions may be used within the scope of the present invention.

Adjoining the body portion 24 is preferably a tapered portion 26. The tapered portion 26 preferably has a taper such that the cross sectional area of the tapered portion 26 reduces from the body portion 24 toward a distal portion 28 at the distal end 16 of the implant 12. The amount of taper of the tapered portion 24 is preferably sufficient to form a shoulder between the body portion 24 and the distal portion 28 to prevent the implant 12 from being inserted too far into the bone as discussed more fully below.

The distal portion 28 may have a substantially cylindrical shaped configuration, or may have a conical configuration with a tapered exterior surface to facilitate insertion of the implant 12 into the bone. An eyelet or opening 30 is preferably formed in the distal portion 28, in a direction transverse to the longitudinal axis 18 for receiving a flexible strand or suture.

Figure 2A:
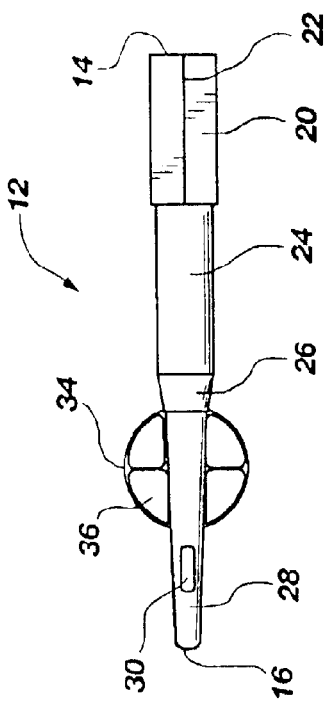
FIG. 2A is a top view of the implant of FIG. 1 as it passes through a cross section of a femoral tunnel.
Figure 2B:
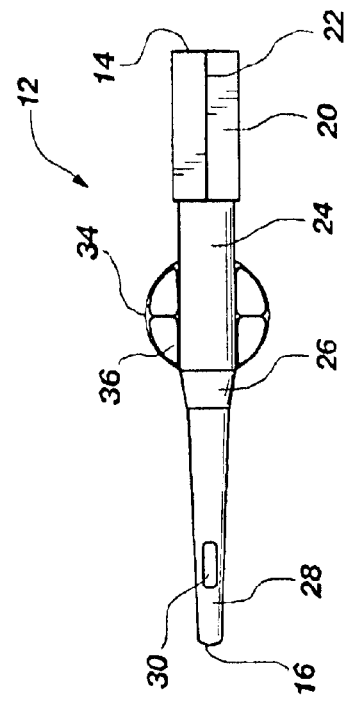
FIG. 2B is a top view of the implant of FIG. 1 as it passes through a cross section of a femoral tunnel, the implant being shown in a position inserted further than the position shown in FIG. 2A.
Figure 2C:
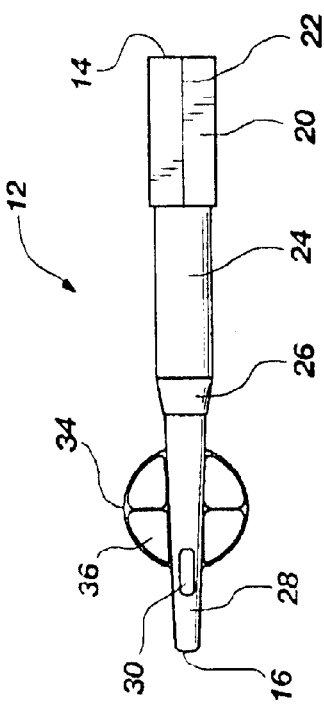
FIG. 2C is a top view of the implant of FIG. 1 as it passes through a cross section of a femoral tunnel, the implant being shown in a position inserted further than the position shown in FIG. 2B.
Figure 2D:
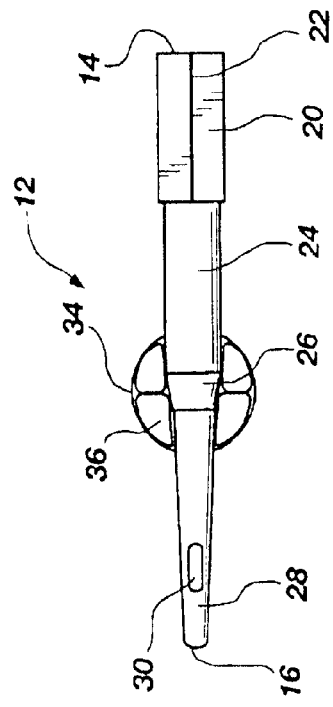
FIG. 2D is a top view of the implant of FIG. 1 as it passes through a cross section of a femoral tunnel, the implant being shown in a position inserted further than the position shown in FIG. 2C.

The importance of the geometric configuration of the implant 12 is illustrated in FIGS. 2A–2D, which show top views of the implant 12 as it progressively passes through a cross section of a femoral tunnel 34 (a description of the femoral tunnel is provided in greater detail below). As shown in FIGS. 2A–2D, the implant 12 is inserted transverse to the femoral tunnel 34 to attach replacement ligaments or soft tissue grafts 36 within the femoral tunnel 34. The replacement ligaments or soft tissue grafts 36 may be formed of any variety of biologic and synthetic materials known to those skilled in the art of reconstructing damaged natural ligaments. As shown in FIG. 2A, the conical distal portion 28 facilitates insertion of the implant 12 through the femoral tunnel 34. As the implant 12 is inserted further within the femoral tunnel 34, as shown in FIG. 2B, the taper of the distal portion 28 causes the soft tissue grafts 36 to be compressed against a sidewall of the femoral tunnel 34. As shown in FIG. 2C, further compression of the soft tissue grafts 36 occurs as the tapered portion 26 and body portion 24 are inserted into the femoral tunnel 34. When the implant 12 is fully inserted within the femoral tunnel 34, as shown in FIG. 2D, the larger diameter of the body portion compresses the soft tissue grafts 36 in place against a sidewall of the femoral tunnel 34, and the tapered portion 26 forms a shoulder which abuts against an annular seat 46 in the receptor bone, as shown in FIGS. 3–5, to prevent the implant 12 from being inserted too far into the receptor bone.

The implant 12 is preferably configured to have a rate of taper from the proximal end 14 to the distal end 16. The rate of taper is defined as the change in radial distance from the center of the implant 12 to the exterior surface of the implant, per unit distance along the longitudinal axis 18. For example, the body portion 24 preferably has a uniform cylindrical cross section and therefore has no taper, whereas the tapered portion 26 has a larger rate of taper than the body portion 24 or the distal portion 28. The higher rate of taper of the tapered portion 26 forms a shoulder that is positioned a predetermined distance from a proximal most end of the body portion 24 to thereby engage in contact against the annular seat 46 formed within the femur 38 and thereby limit an insertion depth of the implant 12.

The implant 12 is preferably configured and dimensioned such that the distal portion 28 and body portion 24 are long enough to extend across the femoral tunnel 34 to facilitate insertion of the implant 12 and provide uniform support of the soft tissue grafts 36. Whereas the tapered portion 26 is configured to be relatively short in comparison with the distal portion 28 and the body portion 24 to form a shoulder between the distal portion 28 and the body portion 24. The shoulder formed by the relatively short tapered portion 26 allows for more control over the fully inserted position of the implant 12. Similarly, the length of the multi-angular portion 20 is configured to provide adequate support to secure the implant 12 within the transverse tunnel 48.

The method of securing ligament replacement into the knee using the implant 12 will be further described by reference to FIGS. 3A–3B, which show diagrammatical views of a femur 38 and a tibia 40 with portions broken away to illustrate flexible strands 42 bringing up soft tissue grafts 36 into the femur 38. Flexible strands 42 may include any variety of surgical filaments known to those skilled in the art. A longitudinal tunnel 44 is formed in the tibia 40 and femur 38 in a manner known to those skilled in the art. The longitudinal tunnel 44 extends into the femur to form the femoral tunnel 34. Also, a transverse tunnel 48 is formed in the femur 38, in a manner described more fully below. Preferably, the transverse tunnel 48 has a smaller diameter than the femoral tunnel 34, and the transverse tunnel 48 penetrates the femoral tunnel 34 at an approximate right angle.

Figure 3A:
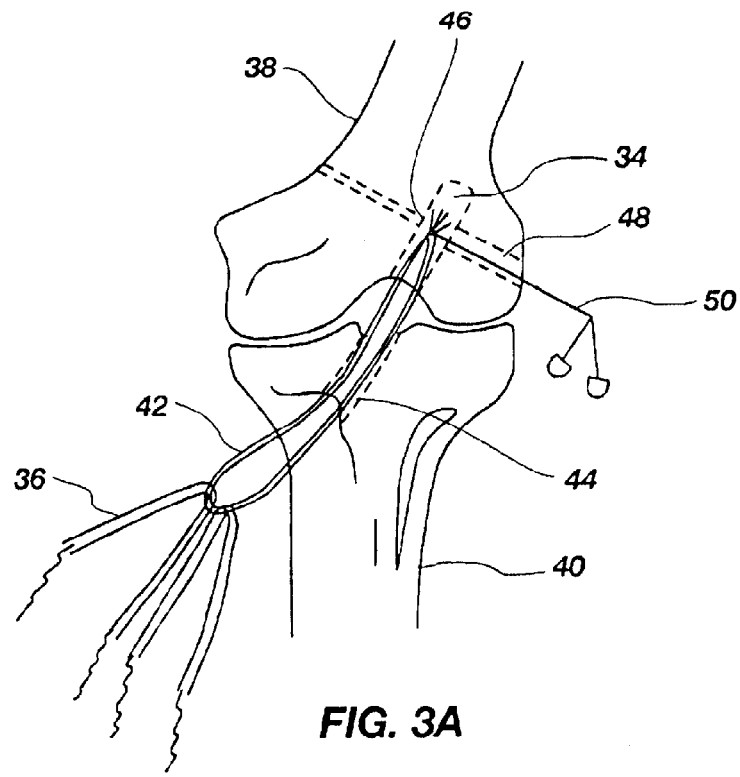
FIG. 3A is a diagrammatical view of a femur and a tibia to illustrate flexible strands bringing up soft tissue grafts into the femur.
Figure 3B:
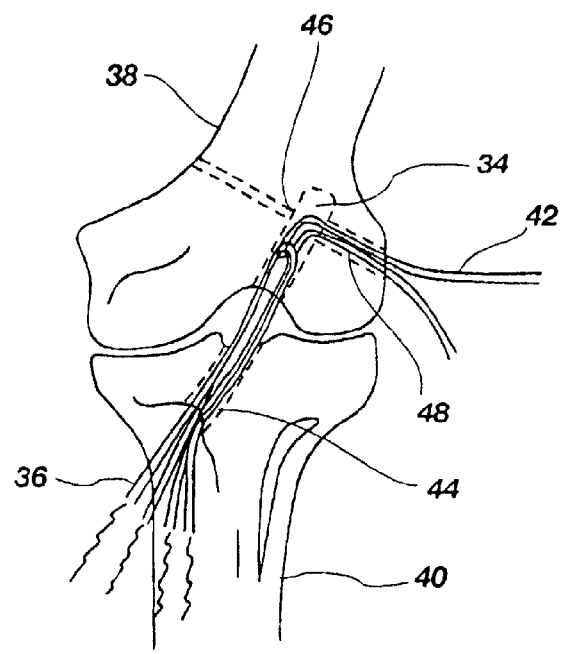
FIG. 3B is a diagrammatical view of a femur and a tibia as in FIG. 3A showing the soft tissue grafts drawn further into the femur.

As shown in FIG. 3A, flexible strands 42 are preferably looped around soft tissue grafts 36 in preparation for ACL reconstruction of the knee. Two flexible strands 42, and two soft tissue grafts 36 are shown in FIG. 3A, however, it will be appreciated that other quantities of strands 42 and soft tissue grafts 36 may be used within the scope of the present invention. The flexible strands 42 are preferably placed retrograde into the femoral tunnel 34 and grasped by an instrument 50 through the transverse tunnel 48 to then be brought outside of the femur 38. Instrument 50 may be any suitable tool known in the art, such as grasping forceps, or a snap on attachment to an arthroscope for example. As shown in FIG. 3B, the soft tissue grafts 36 may be pulled into the femoral tunnel 34 and the flexible strands 42 may exit the femur 38 through the transverse tunnel 48. It will be appreciated that the method described above may be used to position the soft tissue graft 36 in the longitudinal tunnel 44 for securing the soft tissue grafts 36 using staples, implants or any other manner known in the art, within the scope of the present invention.

Figure 4A:
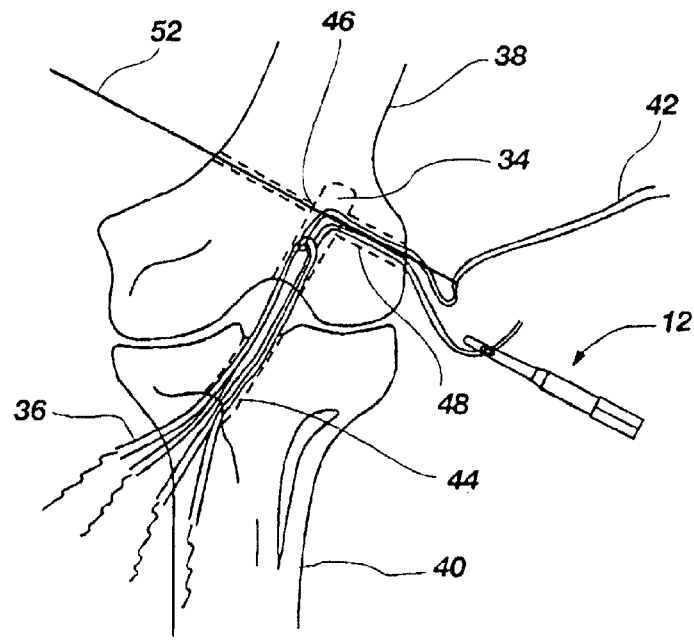
FIG. 4A is a diagrammatical view of a femur and a tibia as in FIG. 3A showing a passing pin driven through the femur to position the implant of FIG. 1.
Figure 4B:
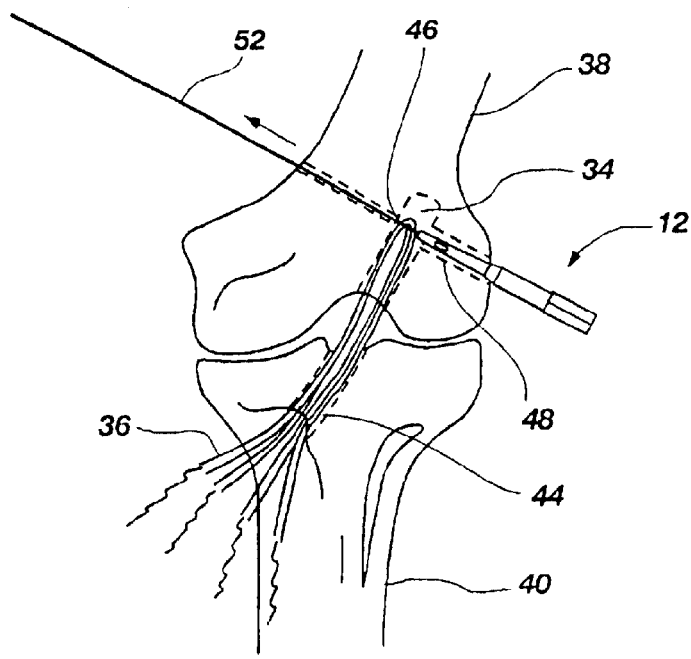
FIG. 4B is a diagrammatical view of a femur and a tibia as in FIG. 4A showing the implant of FIG. 1 entering the transverse tunnel.

Referring now to FIG. 4A, a pair of the flexible strands 42 may be place through the eyelet 30 of the implant 12 and tied into a knot. The other pair of the flexible strands 42 may be passed through an eye of a passing pin or "Beath" pin 52. The passing pin 52 may be driven through the transverse tunnel 48 and out the opposite side of the femur 38. As shown in FIG. 4B, as the flexible strands 42 are pulled away from the implant 12 causing tensioning of the flexible strands 42, the soft tissue grafts 36 may be brought further up into the femoral tunnel 34, and the implant 12 may be pulled into the transverse tunnel 48. The implant 12 may be pulled underneath the soft tissue grafts 36 until the tapered portion 26 makes contact with the annular seat 46 in the femur 38 surrounding the transverse tunnel 48.

Figure 5A:
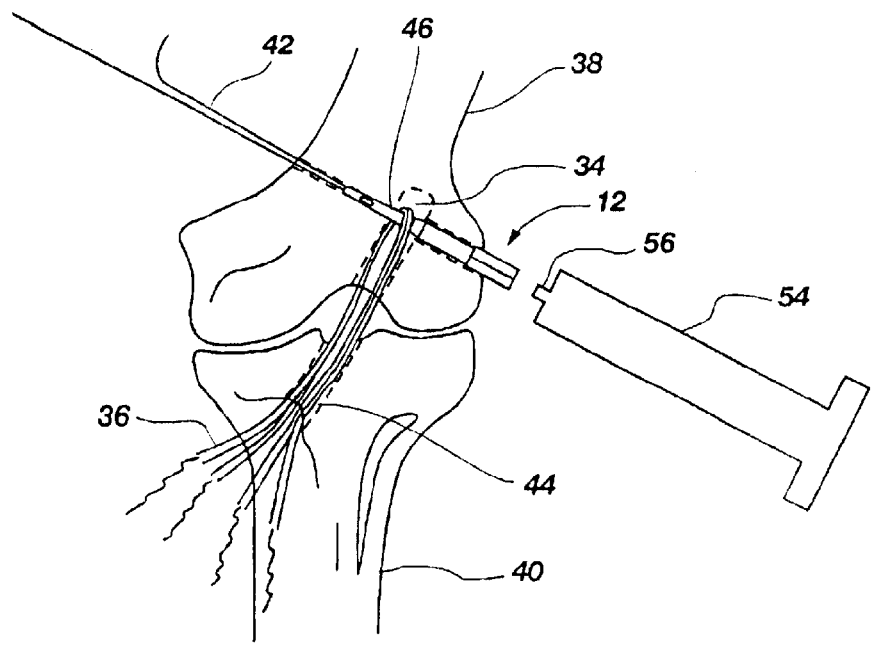
FIG. 5A is a diagrammatical view of a femur and a tibia to illustrate the implant of FIG. 1 being placed in a fully recessed position by an impactor with a projecting tip.
Figure 5B:
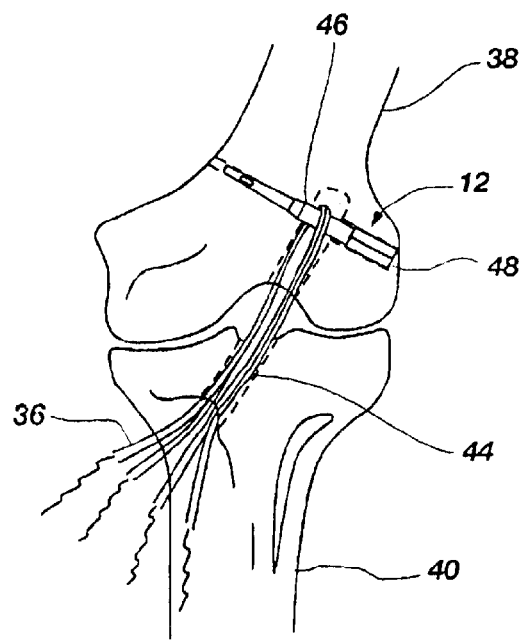
FIG. 5B is a diagrammatical view of a femur and a tibia to illustrate the implant of FIG. 1 placed in a fully recessed position.

As shown in FIG. 5A, a driver or impactor 54 having a projecting tip 56 may be used to seat the implant 12 within the transverse tunnel 48. The projecting tip 56 may be inserted into the fitting 32, as shown most clearly in FIG. 1, to maintain contact between the driver 54 and the implant 12. The driver 54 may be used to force the implant 12 into the transverse tunnel 48 until the implant 12 is fully inserted to the point where the tapered portion 26 contacts the annular seat 46, and where the implant is in a recessed position within the femur 38, as shown in FIG. 5B. It will be appreciated that the driver 54 may be any suitable tool known to those skilled in the art for forcing the implant 12 into the transverse tunnel 48.

Figure 6A:
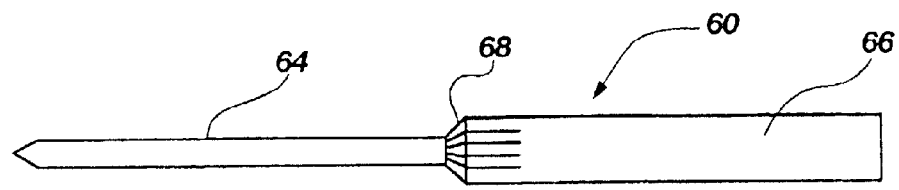
FIGS. 6A and 6B are two different configured drill tips which may be used in accordance with the methods of the present invention.
Figure 6B:
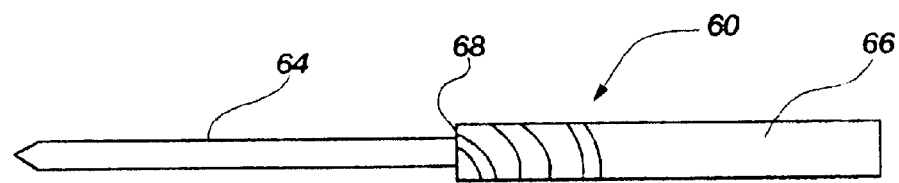
Figure 6C:
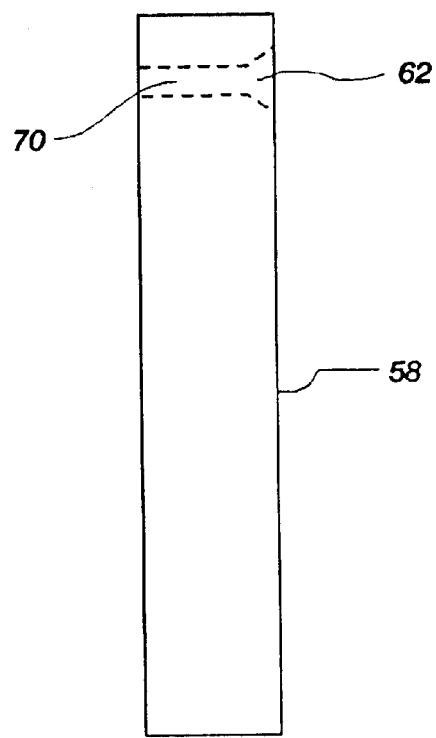
FIG. 6C is a side view of a cannulated drill guide.

Referring now to FIGS. 6A, 6B, and 6C, a side view is shown of a cannulated drill guide 58 and two different embodiments of drill tips, generally indicated at 60, which may be used to form the transverse tunnel 48 in accordance with the principles of the present invention. The drill guide 58 includes an aperture 62 for receiving the drill tip 60 to allow the transverse tunnel 48 to be positioned properly with respect to the femoral tunnel 34. The aperture 62 preferably has a funnel shape to direct the drill tips 60 into the center of the passage 70. The drill tips 60 preferably include a small diameter portion 64 and a larger diameter portion 66 separated by an abutment portion 68. The small diameter portion 64 may be used to drill a portion of the transverse tunnel 48 for receiving the passing pin 52, whereas the larger diameter portion 66 may be used for drilling a portion of the transverse tunnel 48 for receiving the implant 12. The two different diameters of the drill tip 60 allow for different sized portions of the transverse tunnel 48 to be drilled in a single step.

Figure 7A:
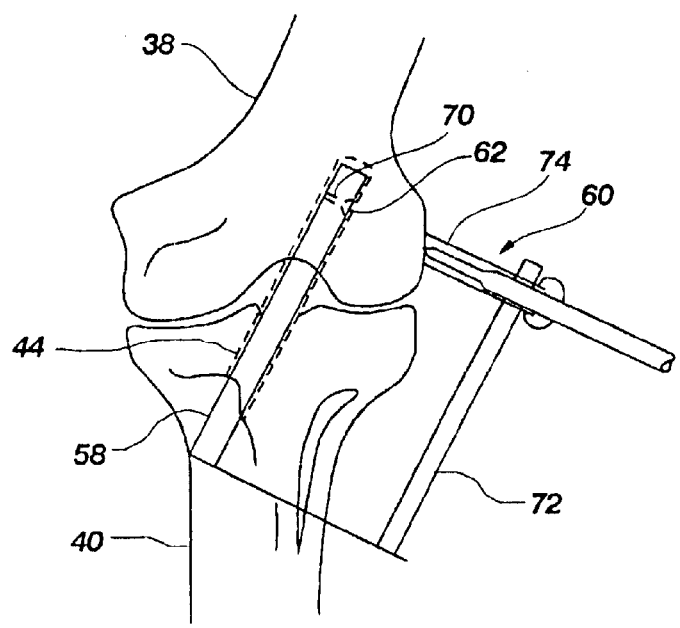
FIG. 7A is a diagrammatical view of a femur and a tibia to illustrate use of the cannulated drill guide during drilling of the femur.
Figure 7B:
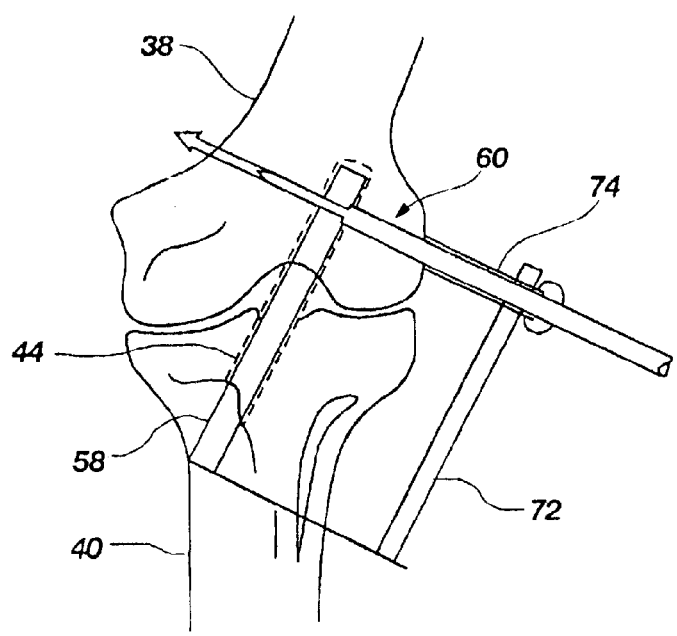
FIG. 7B is a diagrammatical view of a femur and a tibia as shown in FIG. 7A showing the drill extending through the femur.

As shown in FIGS. 7A–7B, the drill guide 58 may be inserted into the longitudinal tunnel 44 and attached to an external drill arm and guide 72. The two step drill 60 may be placed in a guide barrel 74 to ensure that the transverse tunnel 48 is positioned properly. As the drill 60 moves into the femur 38 the funnel shaped aperture 62 guides the drill 60 through the passage 70 until the abutment 68 contacts the drill guide 58 as shown in FIG. 7B. At this point the drill 60 is prevented from extending further into the femur 38 and proper drilling of the transverse tunnel 48 is achieved.

Figure 8A:
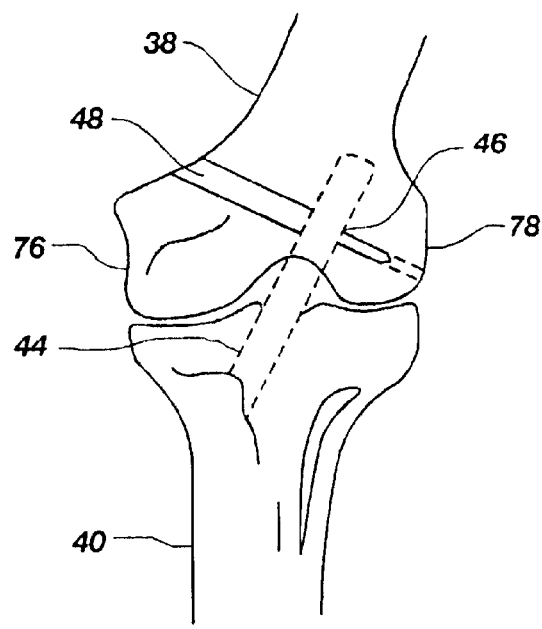
FIG. 8A is a diagrammatical view of a femur and a tibia to illustrate the principles of the present invention may be used in drilling from the medial to the lateral direction (inside of the knee to the outside), which is opposite to the directions as shown in the other figures.
Figure 8B:
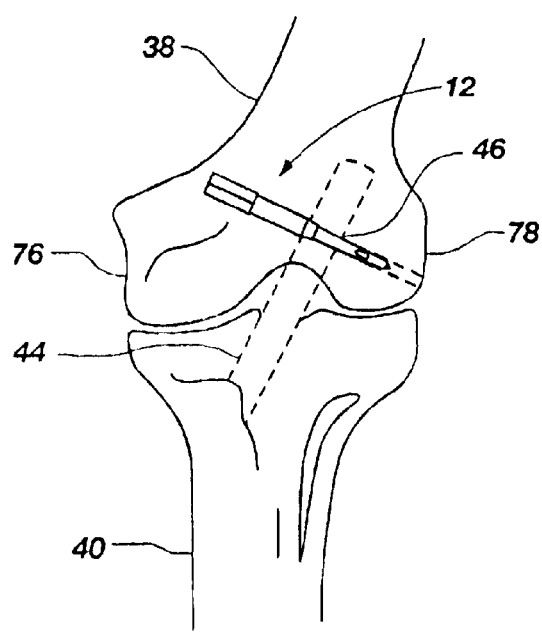
FIG. 8B is a diagrammatical view of a femur and a tibia as illustrated in FIG. 8A, showing the implant of the present invention embedded in the transverse tunnel.

As shown in FIGS. 8A–8B, the principles of the present invention may be used in drilling from the medial side 76 of the femur 38 to the lateral side 78 of the femur 38 (inside of the knee to the outside), which is opposite to the directions as shown in the preceding figures. Therefore, the implant 12 may be installed on the opposite side of the knee as previously discussed.

In the illustrated embodiment of the implant 12, the smaller-dimensioned distal portion 28 facilitates the crossing of the implant 12 across the lumen of the longitudinal tunnel 44, directed with a suture "leash," minimizing interaction of the implant 12 with the replacement ligament 36 until the distal portion 28 has reached the smaller diameter portion of the transverse tunnel 48 on the opposite side of the longitudinal tunnel 44. The larger-dimensioned, cylindrical body portion 24 serves to secure the replacement ligament 36 either by compressing it against the tunnel walls (in the case of a looped material), or by blocking the egress of the replacement ligament (in the case of an attached block of bone). The utility of such an implant can be seen by being applicable for use in either the femur 38 or the tibia 40 and with replacement ligaments made out of soft tissue, bone block attached, or synthetic material.

The method of insertion of this implant is not contemplated by previous methods due to the lack of cannulation in the present implant. The process of developing a transverse tunnel 48 which intersects the precise center of the longitudinal bone tunnel 44 is made possible by the novel cannulated guide 58 and stepped drill 60. The guide 58 is first placed into the longitudinal bone tunnel 44 with the funnel shaped aperture 62 of the transverse cannulation or passage 70 directed towards the transverse drill guide 72 that is aimed at a perpendicular, directly to the center of the longitudinal tunnel 44. A drill tip 60 with an initial smaller diameter portion 64 capable of passing through the transverse cannulation 70 of the guide 58 within the longitudinal tunnel 44, and with sufficient length to broach the opposing cortex of bone combined with the larger diameter portion 66 forming the abutment 68 that stops the progress of the drill once reaching the longitudinal tunnel 44 is used to construct a transverse tunnel 48 of two different bore dimensions with a single pass. The drill tip 60 and cannulated guide 58 are then removed from the bone.

In the illustrated embodiment, the graft 36 may then be brought into the longitudinal tunnel 44 by first looping the graft 36 with a flexible strand 42 and then passing the flexible strand 42 into the longitudinal tunnel 44 in a retrograde fashion. The flexible strand 42 may then be brought out the medial and lateral aspects of the bone using the passing pin 52. The flexible strand 42 may be tensioned by pulling opposing portions of the strand 42 in substantially opposite directions wherein the graft 36 is brought up into the longitudinal tunnel 44 until it sits just above the flexible strand 42 which is now straight in line with the course of the previously constructed transverse tunnel 48. One end of the flexible strand 42 may then be attached to the implant 12 and with or without the use of an impaction instrument 54, the implant 12 may be brought into and across the longitudinal bone tunnel 44 thus securing the replacement ligament 36.

The implant 12 may be either driven flush with the external cortex or cut flush with an appropriate cutting device.

This method and implant can be utilized in either the femur 38 or the tibia 40 and with a variety of replacement ligament types unlike other systems which have been constrained to specific grafts.

It will be appreciated that the structure, apparatus, and methods disclosed herein are merely examples of means for directing and securing a placement ligament into the femur or tibia of the knee, and it should be appreciated that any structure, apparatus or system that perform functions the same as, or equivalent to, those disclosed herein are intended to fall within the scope of a means for directing and securing a placement ligament into the femur or tibia of the knee, including those structures, apparatus or systems that are presently known, or which may become available in the future. Anything which functions the same as, or equivalently to, a means for directing and securing a placement ligament into the femur or tibia of the knee falls within the scope of this element.

In accordance with the features and combinations described above, a preferred method for fixing a replacement ligament within a first tunnel of a bone includes the steps of:

(a) forming a second tunnel in said bone intersecting said first tunnel;

(b) joining said replacement ligament to a strand and inserting said strand into said first tunnel;

(c) accessing said strand from said second tunnel and pulling said stand through said second tunnel to thereby position said replacement ligament into said first tunnel; and (d) securing the replacement ligament in place within said first tunnel.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An implant for securing and positioning a replacement ligament in a bone tunnel of a receptor bone, said implant comprising:
    a multi-angular portion formed at a proximal end of said implant, said multi-angular portion having a polygonal cross section;
    a body portion adjoining said multi-angular portion, said body portion having a uniform cross section;
    a tapered portion adjoining said body portion, said tapered portion tapering in a proximal to distal direction to a smaller cross-sectional area away from said body portion; and
    a distal portion adjoining said tapered portion and extending to a distal end of said implant.

2. The implant of claim 1, wherein said multi-angular portion has a fitting disposed thereon for attaching a driving member.

3. The implant of claim 1, wherein said multi-angular portion forms a plurality of ridges extending substantially parallel to a longitudinal axis of said implant.

4. The implant of claim 3, wherein said multi-angular portion has a radial dimension at said ridges that is greater than a radial dimension of said body portion.

5. The implant of claim 1, wherein said polygonal cross section is substantially square.

6. The implant of claim 1, wherein said body portion is substantially cylindrical having a substantially smooth exterior surface characterized by an absence of helical threads.

7. The implant of claim 1, wherein said distal portion has a tapered configuration.

8. The implant of claim 1, wherein said tapered portion has a length that is less than one fourth a length of said distal portion.

9. The implant of claim 1, further comprising an opening in said distal portion.

10. The implant of claim 9, wherein said opening extends through said distal portion in a direction transverse to a longitudinal axis of said implant.

11. The implant of claim 1, wherein said implant is substantially solid, characterized by an absence of a cannulation along a longitudinal axis of said implant.

12. The implant of claim 1, wherein said multi-angular portion has a substantially square cross section, wherein said body portion is substantially cylindrical, and wherein said distal portion has a tapered configuration.

13. The implant of claim 1, wherein said implant is made of metal.

14. The implant of claim 1, wherein said implant is made of a polymer.

15. The implant of claim 1, wherein said implant is made of a bone material.

16. An implant for securing and positioning a replacement ligament in a bone tunnel of a receptor bone, said implant comprising:
    a multi-angular portion comprising a first end and a second end, said multi-angular portion having a polygonal cross section forming a plurality of longitudinal ridges extending between said first end and said second end;
    a cylindrical body portion adjoining said second end of said multi-angular portion;
    a tapered portion adjoining said body portion, and a distal portion adjoining said tapered portion, said tapered portion forming a shoulder between said body portion and said distal portion;
    wherein a radial dimension of said multi-angular portion at a point between said ridges is substantially the same as a radial dimension of said body portion to facilitate insertion of said multi-angular portion within said receptor bone.

17. The implant of claim 16, wherein a radial dimension of said multi-angular portion at said ridges is greater than said radial dimension of said body portion to allow said multi-angular portion to form an interference fit between said implant and said receptor bone.

18. The implant of claim 16, wherein said multi-angular portion has a fitting disposed thereon for attaching a driving member.

19. The implant of claim 16, wherein said polygonal cross section is substantially square.

20. The implant of claim 16, wherein said distal portion has a tapered configuration such that a cross sectional area of said tapered portion reduces ma direction away from said body portion.

21. The implant of claim 20, wherein said distal portion has an opening extending through said distal portion in a direction transverse to a longitudinal axis of said implant.

22. The implant of claim 16, wherein said body portion has a substantially smooth surface, characterized by an absence of threads, and wherein said body portion is solid characterized by an absence of openings therein.

23. The implant of claim 16, wherein said implant is made of metal.

24. The implant of claim 16, wherein said implant is made of a polymer.

25. The implant of claim 16, wherein said implant is made of a bone material.

26. The implant of claim 16, wherein a substantially smooth interface is formed between said multi-angular portion and said body portion at said point between said ridges.

27. An implant for securing and positioning a replacement ligament in a bone tunnel of a receptor bone, said implant comprising:

a proximal end, a distal end and a longitudinal axis, wherein a cross sectional dimension of said implant at said proximal end is greater than a cross sectional dimension of said implant at said distal end;

a multi-angular portion at said proximal end, said multi-angular portion having a polygonal cross section configured to be inserted within said bone tunnel, said polygonal cross section forming a plurality of ridges extending substantially parallel to said longitudinal axis;

a body portion adjoining said multi-angular portion, said body portion having a substantially uniform cross section, wherein said body portion is substantially cylindrical;

a tapered portion adjoining said body portion, said tapered portion tapering to form a shoulder on said implant between said proximal end and said distal end;

a distal portion adjoining said tapered portion and extending along said longitudinal axis at said distal end of said implant, said distal portion tapering such that a cross section of said distal portion becomes smaller toward said distal end;

said implant having an opening in said distal portion extending through said implant in a direction transverse to said longitudinal axis;

wherein a radial dimension of said multi-angular portion at a point between said ridges is substantially the same as a radial dimension of said body portion to provide a substantially smooth interface between said multi-angular portion and said body portion at said point to facilitate insertion of said multi-angular portion within said receptor bone;

wherein a radial dimension of said multi-angular portion at said ridges is greater than said radial dimension of said body portion to allow said multi-angular portion to form an interference fit between said implant and said receptor bone;

wherein said body portion has a substantially smooth surface, characterized by an absence of threads;

wherein said implant is solid characterized by the absence of a cannulation along said longitudinal axis;

wherein said implant is made of metal;

wherein said polygonal cross section is substantially square;

wherein said tapered portion has a length that is less than one fourth a length of said distal portion;

wherein said multi-angular portion has a fitting disposed thereon for attaching a driving member; and wherein said implant is configured to receive a strand in said opening to position said replacement ligament against said implant for securing said replacement ligament in said bone tunnel.

* * * * *